United States Patent [19]

Kotick et al.

[11] 4,440,931
[45] Apr. 3, 1984

[54] 7β-ARYLALKYL-3-METHOXY OR 3-HYDROXY-4,5α-EPOXY-6β-HYDROXY-7α-HYDROXYMETHYL-17-METHYL OR 17-CYCLOALKYLMETHYLMORPHINANS

[75] Inventors: Michael P. Kotick; David L. Leland; Joseph O. Polazzi, all of Elkhart, Ind.

[73] Assignee: Miles Laboratories, Inc., Elkhart, Ind.

[21] Appl. No.: 416,146

[22] Filed: Sep. 9, 1982

[51] Int. Cl.³ ................. C07D 489/02; A61K 31/485
[52] U.S. Cl. ..................................... 546/44; 424/260; 546/39; 546/45
[58] Field of Search ............................ 546/44, 45, 46; 424/260

[56] References Cited

U.S. PATENT DOCUMENTS 2,178,010 10/1939 Small et al. ............................ 546/74
4,275,205 6/1981 Kotick et al. ........................... 546/44
4,347,361 8/1982 Quick et al. ............................ 546/45

OTHER PUBLICATIONS

Kotick, et al., J. Med. Chem., 24(12), pp. 1445–1450, (1981).
Bentley, et al., J. Am. Chem. Soc., 89(13), pp. 3267–3273, (1967).
Stork, "The Alkaloids", vol. VI, Manske, ed., Academic Press, New York, (1960), p. 226.
Quick, et al., J. Med. Chem., 25(8), pp. 983–986, (1982).

Leland, et al., J. Org. Chem., 48(11), pp. 1813–1819, (1983).
Kotick, et al., J. Med. Chem., 26(7), pp. 1050–1056, (1983).

Primary Examiner—Donald G. Daus
Assistant Examiner—Diana G. Rivers
Attorney, Agent, or Firm—Jerome L. Jeffers

[57] ABSTRACT

Disclosed are 7β-alkyl or arylalkyl-3-methoxy or hydroxy-4,5α-epoxy-6β-hydroxy-7α-hydroxymethyl-17-methyl or cycloalkylmethylmorphinans of the formula:

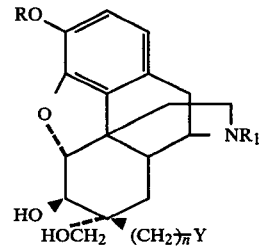

In the above formula, R is H or methyl, $R_1$ is methyl, cyclopropylmethyl or cyclobutylmethyl, n is 2 to 4 and Y is H or phenyl. These compounds are useful as narcotic analgesics.

10 Claims, No Drawings

7β-ARYLALKYL-3-METHOXY OR 3-HYDROXY-4,5α-EPOXY-6β-HYDROXY-7α-HYDROXYMETHYL-17-METHYL OR 17-CYCLOALKYLMETHYLMORPHINANS

BACKGROUND OF THE INVENTION

Morphine is a well-known narcotic analgesic having the structural formula:

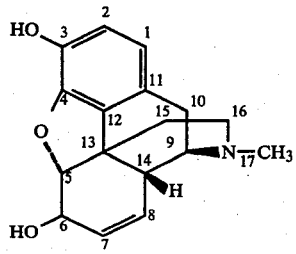

The compounds of this invention are structurally related to morphine and are named according to the morphinan system of nomenclature using the morphinan nucleus as shown below:

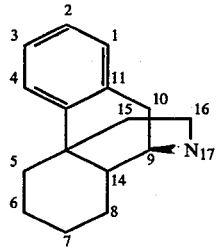

The numbering and the stereochemical placement of atoms in the morphinan system is the same as that depicted for morphine. A dashed line is used to represent a covalent bond projecting below the plane of a reference atom while a wedged or heavily accented line signifies a covalent bond above such plane. The compounds of this invention have the same stereochemical placement of atoms as depicted for the morphine nucleus unless otherwise indicated.

In U.S. Pat. No. 4,275,205, there is disclosed 7,7-ditosyloxymethyl-4,5α-epoxy-3-methoxy-17-methylmorphinan-6β-ols of the formula:

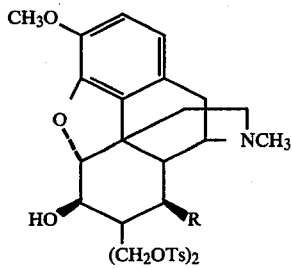

where R is H, $CH_3$ or $CH_2CH_3$. These compounds are precursors for certain 7,7-dimethyl-morphinans having analgesic activity or a combination of analgesic and narcotic antagonist activity.

SUMMARY OF THE INVENTION

The present invention involves 3,7-substituted-4,5α-epoxy-6β-hydroxy-17-methyl or cycloalkylmethylmorphinans of the formula:

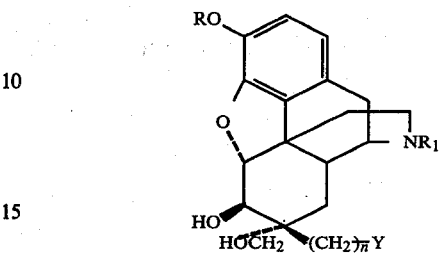

wherein R is H or methyl, $R_1$ is methyl, cyclopropylmethyl or cyclobutylmethyl, n is 2 to 4 and Y is H or phenyl.

DESCRIPTION OF THE INVENTION

The novel morphinan compounds of the present invention are prepared as outlined in scheme I. Referring to scheme I, starting material A (dihydrocodeinone, prepared by the catalytic hydrogenation of codeinone) is treated with formaldehyde in aqueous dioxane solution in the presence of $Ca(OH)_2$ to give 1 as reported (Leland and Kotick, J. Med. Chem., 1981, 24, 717). Reaction of 1 with acetone in the presence of p-toluene sulfonic acid monohydrate and a molecular sieve gives a mixture of major and minor products which are resolved by chromatography. The minor product (obtained in 19% yield) is the 7,7-bis methyleneoxy adduct B which is not further utilized.

The major product 2, obtained in 72% yield as a foam, was shown by various chemical transformations to have the isopropylidene group trans fused between the 6β-hydroxy and 7α-hydroxymethyl positions. The 7β-hydroxymethyl group in the 1,3-dioxolane 2 is oxidized, in 90% yield, to the 7β-formyl derivative 3 using a mixture of dimethyl sulfoxide-trifluoroacetic anhydride in methylene chloride solution at about −60° C. Extention of the chain at the $C_7$ position from the aldehyde 3, is carried out using the Wittig reaction (Maerker, Organic Reactions, 1965, 14, 270). Various triphenylphosphonium ylides are generated from the appropriate halogen salts using either sodium hydride-dimethyl sulfoxide (method of Corey, et al, J. Am. Chem. Soc., 1965, 87, 1345) or phenyl lithium (method of Lambert, et al, J. Am. Chem. Soc., 1977, 99, 3059). The isopropylidene blocking group is removed from the chain extended, unsaturated intermediate 4 by use of dilute HCl in boiling ethanol to give the 7β-unsaturated intermediate 5. When the phenyl lithium method is used to generate the triphenylphosphonium ylide, a side product, namely the tertiary alcohol 6 may also be isolated. This product arises from the reaction of aldehyde 3 directly with the phenyl lithium used to prepare the ylide. Presence of this product indicates incomplete formation of the desired ylide intermediate.

Hydrogenation of 5 over 10% palladium on charcoal in ethanol acidified with concentrated HCl to about pH 2 proceeded slowly. Complete conversion of 5 to 7 could be judged by thin layer chromatography. The 3-0-demethylation of the saturated 3-methoxy compounds 7 to the 3-hydroxy derivatives 8 was accomplished by treatment of 7 with refluxing hydrobromic acid for 10 to 15 minutes. Moderate to good yields of 8 are obtained.

The N-cyclopropylmethyl (P series) or N-cyclobutylmethyl (B series) were prepared by the following sequence. Reaction of N-methyl compounds 7 with cyanogen bromide in chloroform solution in the presence of potassium carbonate gave N-cyano compounds 9. Hydrolysis of the N-cyano compounds 9 to the nor compounds 10 was accomplished by refluxing 9 with 2 N HCl for 8 to 18 hours. Cycloalkylmethylation of 10 to 11 was accomplished by heating 10 with the appropriate cycloalkylmethyl bromide in N,N-dimethylformamide solution containing sodium bicarbonate for 3 to 20 hours until thin layer chromatography indicated completion of the reaction. The 3-methoxy group was cleaved from 11 to give the 3-hydroxy compounds 12 using refluxing HBr as described above.

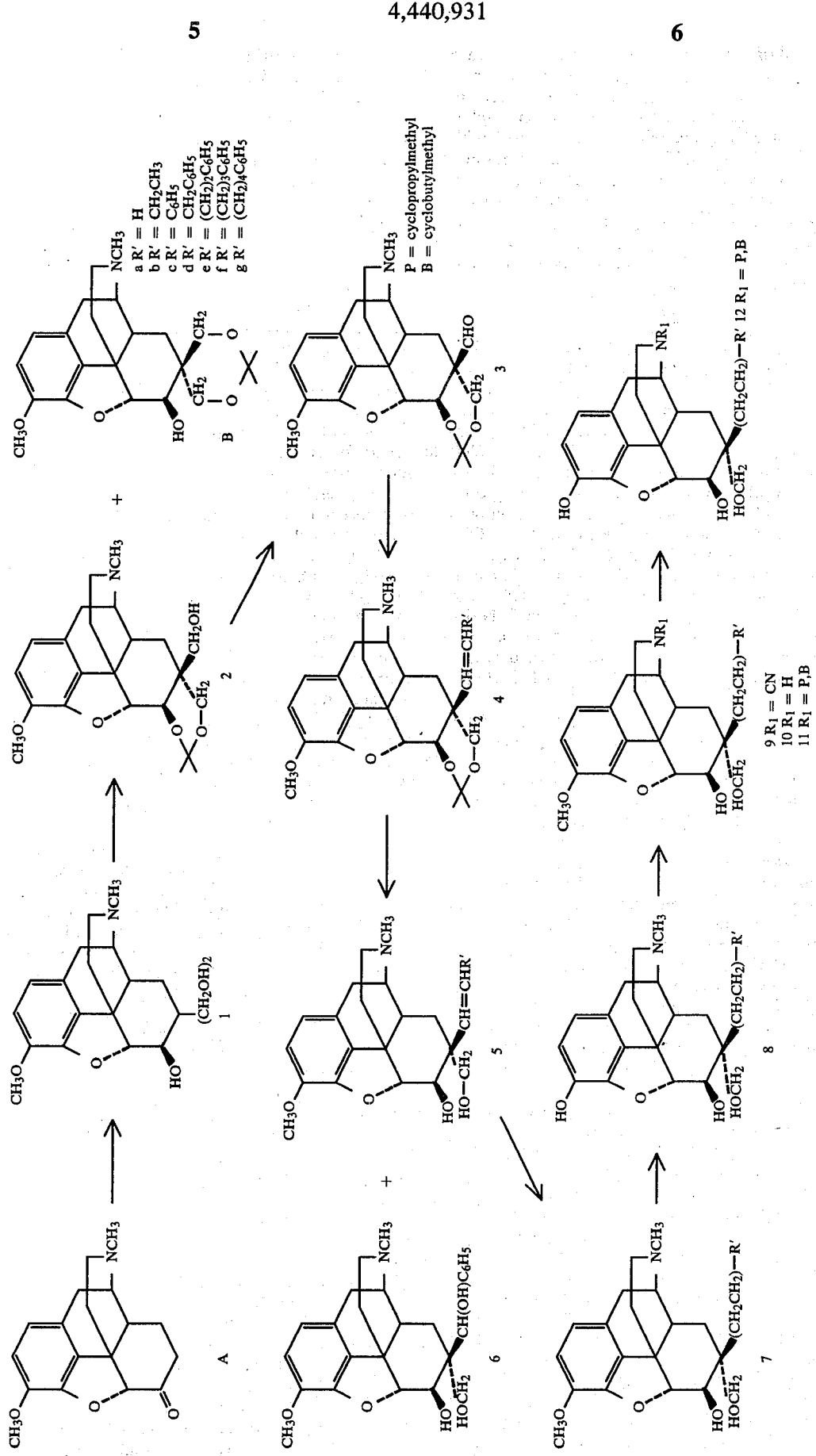

The method of preparing these compounds is further illustrated by the following examples wherein the numbering of compounds corresponds to that used in scheme I and processing in the usual manner implies that the combined organic phases were washed with dilute NH₄OH, dried (MgSO₄), filtered and evaporated at a 40°–45° C. bath temperature, finally under high vacuum. Column chromatography was carried out over silica gel 60 G (E. Merck) using CHCl₃—MeOH mixtures containing 0.25 to 1% v/v concentrated NH₄OH. All compounds gave NMR and mass spectra consistent with the indicated structures.

EXAMPLE I

A. 4,5α-Epoxy-7,7-bis(hydroxymethyl)-6β,7α-O-isopropylidene-3-methoxy-17-methylmorphinan-6β-ol (2) and 4,5α-epoxy-7,7-bis(hydroxymethyl)-7α,7β-O-isopropylidene-3-methoxy-17-methylmorphinan-6β-ol (B)

A mixture of the free base of 1 (10.45 g, 28.9 mmole) and pTsOH.H₂O (6.05 g, 28.9 mmole) in acetone (200 ml) was stirred for 16 hrs. at room temperature. Molecular sieve (4 Å, 25 g) was then added and stirring continued for an additional 24 hrs. The suspension was made basic by the addition of concentrated NH₄OH, filtered and the filtrate evaporated. The residue was partitioned between H₂O and CHCl₃ and further processed to a foam which was chromatographed. First eluted was 2.20 g (19%) of a minor product B NMR δ1.38 (d, 6H, gem CH₃'s, J=7 Hz). Continued elution followed by pooling of appropriate fractions and evaporation gave 8.40 g (72%) of 2 as a foam; NMR δ1.33 (d, 6H, gem CH₃'s, J=8 Hz).

B. 4,5α-Epoxy-7β-formyl-7α-hydroxymethyl-6β,7α-O-isopropylidene-3-methoxy-17-methylmorphinan-6β-ol (3)

To an oxidation mixture prepared from DMSO (7.2 ml, 101.8 mmole) in CH₂Cl₂ (80 ml) and TFAA (10.8 ml, 76.4 mmole) in CH₂Cl₂ (30 ml) was added 2 (20.0 g, 50 mmole) in CH₂Cl₂ (400 ml) slowly over a period of 1 hr. After stirring in the dry ice-acetone bath for 1 hr., TEA (20 ml) was added dropwise and the mixture allowed to warm to room temperature. The solution was evaporated, the residue diluted with H₂O and NH₄OH and extracted with CHCl₃. Processing in the usual fashion gave 18.0 g (90%) of 3 as a solid residue. Recrystallization from EtOAc-hexane gave 14.4 g of crystals, mp 157°–163° C. Recrystallization from the same solvent pair gave an analytical sample of 3, mp 169°–171° C.; NMR δ9.86 (broad s, —CHO), 4.98 (d, 1H, H5, J=6 Hz), 3.90 (CH₃O—), 2.40 (CH₃N—), 1.36 (s, 6H, gem CH₃'s).

Anal. Calcd. for C₂₃H₂₉NO₄: C, 69.15; H, 7.32; N, 3.51. Found: C, 69.24; H, 7.28; N, 3.33.

C. 4,5α-Epoxy-7α-hydroxymethyl-3-methoxy-17-methyl-7β-arylalkylidenemorphinan-6β-ols (5)

Method A-A suspension of 50% NaH (0.66 g, 13.8 mmole) in mineral oil was washed 3 times with hexane while under an argon atmosphere. Dimethylsulfoxide (DMSO) (10 ml) was added and the mixture heated at 60°–70° C. until the evolution of H₂ ceased (ca. 30 min.). The mixture was cooled to 25° C. and the appropriate phosphonium salt (13.8 mmole) in DMSO (50 ml) added dropwise. After 10 min., 3 (5.0 g, 12.5 mmole) in DMSO (50 ml) was added rapidly dropwise. Stirring was continued for 30 min. at room temperature followed by heating of the mixture at 65°–70° C. for 30 min. The cooled mixture was diluted with water and extracted with toluene. The organic phase was evaporated and the residue, consisting of 4 and (C₆H₅)₃PO dissolved in EtOH (200 ml) and 1 NHCl (50 ml) added. The mixture was gently boiled on the steam bath for 30 min. and then evaporated to a small volume. The acidic concentrate was diluted with H₂O and washed several times with toluene. The aqueous solution was then made basic with concentrated NH₄OH and further processing carried out as described below.

Method B-To a suspension of the phosphonium salt (23 mmole) in Et₂O (200 ml), under argon at room temperature, was added phenyl lithium (23 mmole, 1.9 M solution in 7:3 C₆H₆-Et₂O) and the mixture stirred for 1–2 hrs. A solution of 3 (4.0 g, 10 mmole) in 1:1 toluene-Et₂O (100 ml) was added to the dark solution and stirring continued for 2 hrs. The reaction was quenched by the addition of H₂O, concentrated NH₄OH added and the intermediate 4 extracted with CHCl₃. Evaporation of the organic phase was followed by the addition of EtOH and 1 N HCl, the mixture boiled for 30 min., and then further processed as described below.

Compound 5a was prepared by Method A. Crystals of 5a precipitated from the basic aqueous solution and were obtained in 78% yield. Recrystallization from H₂O gave pure 5a, mp 181°–182° C. Anal. (C₂₁H₂₁—NO₄). Intermediate 5b was prepared by Method B and was not further purified, but directly hydrogenated to 7b. In a similar manner, 5c was prepared by Method A and purified by chromatography to give an 89% yield of the desired product as a foam. Compound 5d was prepared by Method B and purified by chromatography to give a 38% yield of 5d as a foam. The HCl salt, mp dec >280° C., was obtained in crystalline form from EtOH. Anal. (C₂₈H₃₃NO₄.HCl). The intermediate analogous to 5e was prepared by Method A using cinnamyl triphenylphosphonium chloride. The di-unsaturated 4-phenyl-1,3-butadieneyl intermediate was not isolated but directly reduced to 7e. Compound 5g was prepared by Method B and obtained as a foam, after chromatography, in 68% yield. Crystallization from EtOH gave pure 5g, mp 168°–170° C. Anal. (C₃₀H₃₇NO₄). 5h was prepared by Method A and purified by chromatography to give a 70% yield of 5h as a foam. The HCl salt, mp dec >260° C., was obtained in crystalline form from EtOH. Anal. (C₃₁H₃₉NO₄.HCl).

D. 4,5α-Epoxy-7β-(α-hydroxybenzyl)-7α-hydroxymethyl-3-methoxy-17-methylmorphinan-6β-ol (6)

This compound was obtained as a side product in the preparation of 5 by Method B. Material obtained by chromatography from several reactions, which migrated as a single spot on TLC, was combined and crystallized from MeOH-EtOAc to give a sample of pure 6, mp 265°–267° C. Anal. (C₂₆H₃₁NO₅).

E. 7β-Arylalkyl-4,5α-epoxy-7α-hydroxymethyl-3-methoxy-17-methylmorphinan-6β-ols (7)

Hydrogenation of 5, as the free base or HCl salt, was carried out over 10% Pd/C (10–25% w/w) at 50 psi in aqueous EtOH acidified with HCl (ca. pH 2) until the uptake of H₂ ceased (2–24 hrs.). After removal of the catalyst by filtration, the filtrate was evaporated to a crystalline residue. In cases where crystallization did not occur, the HCl salt was converted to the free base and further purification carried out by chromatography or crystallization as indicated in table III.

F. 7β-Arylalkyl-4,5α-epoxy-3-hydroxy-7α-hydroxymethyl-17-methylmorphinan-6β-ols (8)

A mixture of 7 (free base or HCl salt) and concentrated HBr (1.0 g in 10–15 ml) was immersed in a preheated oil bath (ca. 140° C.) and refluxed for 10 to 20 min. The reaction mixture was cooled, diluted with H₂O and adjusted to pH 10-11 by the addition of concentrated NH₄OH. The basic solution was extracted with 3 portions of CHCl₃, the organic extracts processed in the usual manner and the residue chromatographed. Crystals of the free base or HCl salt were obtained from the solvents indicated in table III.

G. 7β-Arylalkyl-17-cyano-4,5α-epoxy-7α-hydroxymethyl-3-methoxymorphinan-6β-ols (9)

To a rapidly stirred mixture of 7 (1.0 equiv.) in CHCl₃ (1 g in 15 ml) containing K₂CO₃ (1.5 equiv.) was added dropwise a solution of BrCN (1.2 equiv.) in CHCl₃ (1 g in 15 ml). The mixture was stirred at room temperature for 30 min. and then refluxed for 2 hrs. The insoluble material was removed by filtration and the filtrate evaporated. The residue was evaporated with EtOH until a foam formed. This foam, obtained in nearly quantitative yield and homogenous by TLC, was hydrolyzed to 10 as described below.

H. 7β-Arylalkyl-4,5α-epoxy-7α-hydroxymethyl-3-methoxymorphinan-6β-ols (10)

A mixture of 9 and 2 N HCl (1 g in 15-25 ml) was refluxed for 8 to 18 hrs. The solution was cooled, made basic by the addition of concentrated NH₄OH and extracted with CHCl₃. Processing of the CHCl₃ extracts in the usual fashion was followed by chromatography to give the following 10 as foams, yield being based on the —NCH₃ compounds 7; 10c, 88%; 10d, 81%; 10f, 75%; 10g, 67%. These foams were used in alkylation reactions described below.

I. 7β-Arylalkyl-17-(cycloalkylmethyl)-4,5α-epoxy-7α-hydroxymethyl-3-methoxymorphinan-6β-ols (11P,B).

A solution of 10 in DMF (1 g in 20 ml) containing NaHCO₃ (2.5 equiv.) and cycloalkylmethyl bromide (1.2 equiv.) was heated in an oil bath at 100° C. while under argon until the reaction was complete as indicated by TLC (3-20 hrs.). The mixture was cooled and filtered to remove insolubles. The filtrate was evaporated using an oil pump and the residue dissolved in H₂O. This mixture was adjusted to pH 10-11 with NH₄OH and extracted with 3 portions of toluene. The organic phase was processed in the usual manner, the residue chromatographed and the product crystallized as the free base or HCl salt as indicated in table III.

J. 7β-Arylalkyl-17-(cycloalkylmethyl)-4,5α-epoxy-3-hydroxy-7α-hydroxymethyl-morphinan-6β-ols (12P,B)

A suspension of the 3-methoxy compound 11 in 48% HBr (1 g in 10 ml) was placed in a preheated, 140° C. oil bath and the mixture refluxed for 10-20 min. The cooled solution was diluted with H₂O and made basic with NH₄OH. This was extracted with EtOAc or CHCl₃, the organic extracts processed in the usual fashion and the residue chromatographed. Pure 12 was crystallized as the free base or HCl salt. Further details are given in table III.

PHARMACOLOGICAL EVALUATION

Analgesic effects of the test compounds were determined in mice by use of the acetic acid induced writhing test described by B. A. Whittle, Brit. J. Pharmacol., 22:246 (1964). In this test, at least 3 groups of 5 male CD-1 mice each were given subcutaneous doses of the test drug dissolved in distilled water. In all cases, 0.4 ml of a 0.5% v/v acetic acid in distilled water solution was administered intraperitoneally 15 min. post drug. The number of writhes in a 20 min. interval beginning 5 min. after the acetic acid injection were determined and compared with the number of writhes in a control group which had received only acetic acid.

Percent inhibition of writhing was calculated as:

$$\% \text{ inhibition} = \frac{\text{No. Control Writhes} - \text{No. Treated Writhes}}{\text{No. Control Writhes}}$$

The ED₅₀ dose, i.e., the dose required to reduce the number of writhes by 50%, was determined graphically from a plot of % inhibition as a probit verus log dose. Confidence limits of 95% were calculated on the basis of those results falling in the range 16-84% inhibition. See Lichtfield, J. T. and Wilcoxson, F., J. Pharmacol. Exp. Ther., 96, 99-113 (1949).

The results of this evaluation are set out in table I.

TABLE I

Narcotic Agonist Activity-Mouse Writhing Assay, s.c. Injection For N—Methyl Compounds

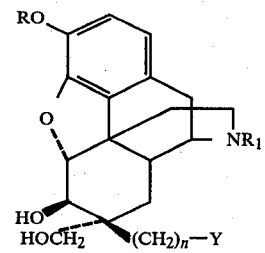

| Compound | R | R₁ | n | Y | ED₅₀ (μ mole/kg) | ED₅₀ (mg/kg) |
|---|---|---|---|---|---|---|
| 7a* | CH₃ | CH₃ | 2 | H | 2.7 | 1.05 |
| 7b* | CH₃ | CH₃ | 4 | H | 13.7 | 5.8 |
| 7c | CH₃ | CH₃ | 2 | Ph | 0.028** | 0.012 |
| 7d* | CH₃ | CH₃ | 3 | Ph | 0.39 | 0.19 |
| 7e | CH₃ | CH₃ | 4 | Ph | 0.014 | 0.0066 |
| 7f | CH₃ | CH₃ | 5 | Ph | 2.3 | 1.19 |
| 7g | CH₃ | CH₃ | 6 | Ph | 4.5 | 2.2 |
| 8b | H | CH₃ | 4 | H | 0.56 | 0.21 |
| 8c | H | CH₃ | 2 | Ph | 0.004 | 0.0016 |
| 8d | H | CH₃ | 3 | Ph | 0.85 | 0.37 |
| 8e | H | CH₃ | 4 | Ph | 0.003 | 0.0014 |
| 8f* | H | CH₃ | 5 | Ph | 12.0 | 6.0 |
| 8g* | H | CH₃ | 6 | Ph | >19 | >10 |
| codeine | | | | | 10.3 | 4.2 |
| morphine | | | | | 2.1 | 0.79 |
| dihydrocodeinone | | | | | 2.4 | 1.06 |
| dihydromorphinone | | | | | 0.25 | 0.08 |

*HCl salt
**Repeat 0.014/.0062

TABLE II

Narcotic Agonist Activity-Mouse Writhing Assay, s.c. Injection For N—Cycloalkylmethyl Compounds

| Compound | R | R₁ | n | Y | ED₅₀ (μ mole/kg) | ED₅₀ (mg/kg) |
|---|---|---|---|---|---|---|
| 11Pc* | CH₃ | P | 2 | Ph | 0.61 | 0.31 |
| 11Pd | CH₃ | P | 3 | Ph | 0.13 | 0.065 |
| 11Pe | CH₃ | P | 4 | Ph | 0.22 | 0.12 |
| 11Pf* | CH₃ | P | 5 | Ph | 0.40 | 0.22 |
| 11Bc* | CH₃ | B | 2 | Ph | 0.70 | 0.37 |
| 11Bd | CH₃ | B | 3 | Ph | 0.04 | 0.019 |
| 11Be* | CH₃ | B | 4 | Ph | 0.52 | 0.27 |
| 11Bf* | CH₃ | B | 5 | Ph | 0.30 | 0.17 |
| 12Pc | H | P | 2 | Ph | 0.95 | 0.44 |
| 12Pd* | H | P | 3 | Ph | 0.47 | 0.24 |
| 12Pe | H | P | 4 | Ph | 11.0 | 5.4 |
| 12Pf* | H | P | 5 | Ph | >19 | >10 |
| 12Bc | H | B | 2 | Ph | 2.5 | 1.21 |
| 12Bd* | H | B | 3 | Ph | 0.57 | 0.30 |
| 12Be* | H | B | 4 | Ph | 21.3 | 11.5 |

TABLE II-continued

Narcotic Agonist Activity-Mouse Writhing Assay, s.c. Injection For N—Cycloalkylmethyl Compounds

| Compound | R | $R_1$ | n | Y | $ED_{50}$ ($\mu$ mole/kg) | $ED_{50}$ (mg/kg) |
|---|---|---|---|---|---|---|
| 12Bf* | H | B | 5 | Ph | >10 | >10 |

*HCl salt
P = cyclopropylmethyl
B = cyclobutylmethyl

TABLE III

6β-Hydroxy-7α-Hydroxymethyl-α-Substituted Morphinans

| Compound | % Yield | mp, °C. | Recyrstn Solvent[a] |
|---|---|---|---|
| 7a | 58[b] | 200–204 | E |
| 7b | 53[b] | >270 | E |
| 7c | 72[c] | 240–242 | E |
| 7d | 81[b] | 267–270 | M—EA |
| 7e | 89[d] | 196–198 | EA—C |
| 7f | 83[b] | 200–202 | M—EA |
| 7g | 67[c] | 160–161 | E |
| 8b | 81[c] | 224–226 | M—EA |
| 8c | 54[c] | 259–262 | M—EA |
| 8d | 62[c] | 240–245 | E |
| 8e | 82[c] | 192–193 | EA |
| 8f | 88[c] | 212–216 | M—EA |
| 8h | 67[c] | 249–251 | E |
| 11Pc | 85[c] | 261–264 | E |
| 11Pd | 44[e] | 198–199.5 | E |
| 11Pe | 63[c] | 256–258 | M—EA |
| 11Pf | 75[c] | 240–243 | E |
| 11Bc | 74[c] | 200[f] | E |
| 11Bd | 62[c] | 152–154 | EA |
| 11Be | 62[c] | 256–258 | M—EA |
| 11Bf | 77[c] | 247–250 | E |
| 12Pc | 34[c] | 252–254 | E |
| 12Pd | 36[c] | dec >200 | M—EA |
| 12Pe | 86[c] | 214–216 | E—A |
| 12Pf | 57[c] | 168–174 | M—EA |
| 12Bc | 77 | 255–257 | E |
| 12Bd | 49 | >280 | M—EA |
| 12Bf | 95 | 222–225 | M—EA |
| 12Bf | 93 | 182–186 | M—EA |

[a]C = chlorofoam; E = ethanol; EA = ethyl acetate; M = methanol; W = water.
[b]HCl salt crystallized directly.
[c]Yield of free base after chromatography.
[d]Free base crystallized directly.
[e]Directly crystallized from toluene.
[f]Softens

TABLE IV

ELEMENTAL ANALYSES

| Compound | Formula | % C | % H | % N | |
|---|---|---|---|---|---|
| 5a | $C_{21}H_{27}NO_4$ | 70.56 | 7.61 | 3.92 | Calc. |
| | | 70.58 | 7.60 | 3.59 | Found |
| 5d | $C_{28}H_{33}NO_4.HCl$ | 69.48 | 7.08 | 2.89 | |
| | | 69.23 | 7.22 | 2.78 | |
| 5f | $C_{30}H_{37}NO_4$ | 75.76 | 7.84 | 2.94 | |
| | | 75.54 | 7.57 | 2.64 | |
| 5g | $C_{31}H_{39}NO_4.HCl$ | 70.77 | 7.66 | 2.66 | |
| | | 71.14 | 7.30 | 2.64 | |
| 6 | $C_{26}H_{31}NO_5$ | 71.37 | 7.14 | 3.20 | |
| | | 71.34 | 7.37 | 3.27 | |
| 7a | $C_{21}H_{29}NO_4.HCl$ | 63.71 | 7.64 | 3.54 | |
| | | 63.69 | 7.99 | 3.41 | |
| 7b | $C_{23}H_{33}NO_4.HCl$ | 65.16 | 8.08 | 3.30 | |
| | | 65.22 | 8.15 | 3.32 | |
| 7c | $C_{27}H_{33}NO_4$ | 74.45 | 7.64 | 3.22 | |
| | | 74.25 | 7.80 | 3.26 | |
| 7d | $C_{28}H_{35}NO_4.HCl$ | 69.19 | 7.46 | 2.88 | |
| | | 69.25 | 7.67 | 2.78 | |
| 7e | $C_{29}H_{37}NO_4$ | 75.13 | 8.04 | 3.02 | |
| | | 74.96 | 7.96 | 2.92 | |
| 7f | $C_{30}H_{39}NO_4.HCl$ | 70.09 | 7.84 | 2.72 | |
| | | 69.69 | 7.98 | 2.74 | |
| 7g | $C_{31}H_{41}NO_4$ | 75.73 | 8.41 | 2.85 | |
| | | 74.64 | 8.54 | 2.82 | |
| 8b | $C_{22}H_{31}NO_4$ | 70.75 | 8.37 | 3.75 | |

TABLE IV-continued

ELEMENTAL ANALYSES

| Compound | Formula | % C | % H | % N |
|---|---|---|---|---|
| | | 70.94 | 8.44 | 3.63 |
| 8c | $C_{26}H_{31}NO_4$ | 74.08 | 7.41 | 3.32 |
| | | 73.80 | 7.46 | 3.38 |
| 8d | $C_{27}H_{33}NO_4$ | 74.45 | 7.64 | 3.22 |
| | | 74.20 | 7.77 | 3.14 |
| 8e | $C_{28}H_{35}NO_4$ | 74.80 | 7.85 | 3.12 |
| | | 74.56 | 7.83 | 2.95 |
| 8f | $C_{29}H_{37}NO_4.HCl$ | 69.65 | 7.66 | 2.80 |
| | | 69.87 | 7.39 | 2.59 |
| 8h | $C_{30}H_{39}NO_4.HCl.H_2O$ | 67.72 | 7.95 | 2.63 |
| | | 67.67 | 8.14 | 2.57 |
| 11Pc | $C_{30}H_{37}NO_4.HCl$ | 70.36 | 7.48 | 2.74 |
| | | 70.32 | 7.46 | 2.85 |
| 11Pd | $C_{31}H_{39}NO_4$ | 76.04 | 8.03 | 2.86 |
| | | 75.88 | 7.82 | 2.63 |
| 11Pe | $C_{32}H_{41}NO_4.HCl$ | 71.16 | 7.84 | 2.59 |
| | | 70.84 | 7.81 | 2.42 |
| 11Pf | $C_{33}H_{43}NO_4.HCl$ | 71.52 | 8.00 | 2.53 |
| | | 71.38 | 7.81 | 2.53 |
| 11Bc | $C_{31}H_{39}NO_4.HCl$ | 70.77 | 7.66 | 2.66 |
| | | 70.44 | 7.66 | 2.79 |
| 11Bd | $C_{32}H_{41}NO_4$ | 76.31 | 8.20 | 2.78 |
| | | 76.12 | 8.24 | 2.61 |
| 11Be | $C_{33}H_{43}NO_4.HCl$ | 71.52 | 8.00 | 2.53 |
| | | 71.16 | 7.73 | 2.47 |
| 11Bf | $C_{34}H_{45}NO_4.HCl$ | 71.87 | 8.16 | 2.46 |
| | | 71.53 | 8.13 | 2.53 |
| 12Pc | $C_{29}H_{35}NO_4$ | 75.46 | 7.64 | 3.03 |
| | | 75.18 | 7.70 | 2.90 |
| 12Pd | $C_{30}H_{37}NO_4.HCl$ | 70.36 | 7.48 | 2.74 |
| | | 70.10 | 7.65 | 2.85 |
| 12Pe | $C_{31}H_{39}NO_4$ | 76.04 | 8.03 | 2.86 |
| | | 76.20 | 8.12 | 2.80 |
| 12Pf | $C_{32}H_{41}NO_4.HCl$ | 71.16 | 7.84 | 2.59 |
| | | 70.69* | 7.85 | 2.57 |
| 12Bc | $C_{30}H_{37}NO_4$ | 75.76 | 7.84 | 2.94 |
| | | 75.62 | 7.93 | 2.76 |
| 12Bd | $C_{31}H_{39}NO_4.HCl$ | 70.77 | 7.66 | 2.66 |
| | | 70.98 | 7.78 | 2.62 |
| 12Be | $C_{32}H_{41}NO_4.HCl$ | 71.16 | 7.84 | 2.59 |
| | | 71.23 | 7.67 | 2.25 |
| 12Bf | $C_{33}H_{43}NO_4.HCl$ | 71.52 | 8.00 | 2.53 |
| | | 71.84 | 8.01 | 2.30 |

The compounds claimed herein, especially those with small $ED_{50}$ values, are very potent narcotic agonists. As such, they are useful for the relief of pain, for pre-operative anesthesia or for the immobolization of large animals. The dose to be administered to achieve the desired result, i.e., the effective dose, may vary from individual to individual but is readily determined by one skilled in the art without undue experimentation.

The compounds of the present invention form pharmacologically active addition salts with organic acids. Typical acid addition salts are the tartrate and maleate. These compounds may be administered by known conventional methods such as intravenous, parenteral, buccal, rectal or oral routes. Dose forms for the administration of these compounds can be prepared by methods recognized in the pharmaceutical sciences.

What is claimed is:

1. 7β-alkyl or arylalkyl-3-methoxy or hydroxy-4,5α-epoxy-6β-hydroxy-7α-hydroxymethyl-17-methyl or cycloalkylmethylmorphinans characterized by the formula:

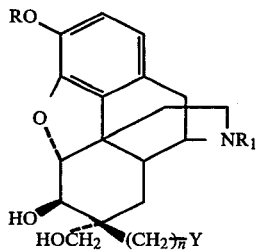

wherein R is H or methyl, R₁ is methyl, cyclopropylmethyl or cyclobutylmethyl, n is 2 to 4 and Y is H or phenyl.

2. The morphinans of claim 1 wherein R is methyl, R₁ is cyclobutylmethyl or cyclopropylmethyl, n is 5 and Y is phenyl.

3. The morphinans of claim 1 wherein n is 2 to 4 and Y is phenyl.

4. A morphinan as characterized by claim 1 wherein R is CH₃, R₁ is methyl, n is 2 and Y is phenyl.

5. A morphinan as characterized by claim 1 wherein R is CH₃, R₁ is methyl, n is 4 and Y is phenyl.

6. A morphinan as characterized by claim 1 wherein R is H, R₁ is methyl, n is 2 and Y is phenyl.

7. A morphinan as characterized by claim 1 wherein R is H, R₁ is methyl, n is 4 and Y is phenyl.

8. A morphinan as characterized by claim 1 wherein R is CH₃, R₁ is cyclopropylmethyl, n is 3 and Y is phenyl.

9. A morphinan as characterized by claim 1 wherein R is CH₃, R₁ is cyclobutylmethyl, n is 3 and Y is phenyl.

10. A morphinan as characterized by claim 1 wherein R is CH₃, R₁ is cyclobutylmethyl, n is 5 and Y is phenyl.

* * * * *